US008003080B2

(12) United States Patent
Rabinowitz et al.

(10) Patent No.: US 8,003,080 B2
(45) Date of Patent: *Aug. 23, 2011

(54) DELIVERY OF DRUG AMINES THROUGH AN INHALATION ROUTE

(75) Inventors: Joshua D. Rabinowitz, Mountain View, CA (US); Alejandro C. Zaffaroni, Atherton, CA (US)

(73) Assignee: Alexza Pharmaceuticals, Inc., Mountain VIew, CA (US)

( * ) Notice: Subject to any disclaimer, the term of this patent is extended or adjusted under 35 U.S.C. 154(b) by 317 days.

This patent is subject to a terminal disclaimer.

(21) Appl. No.: 10/437,643

(22) Filed: May 13, 2003

(65) Prior Publication Data

US 2004/0009128 A1 Jan. 15, 2004

Related U.S. Application Data

(60) Provisional application No. 60/380,819, filed on May 13, 2002.

(51) Int. Cl.
*A61K 9/12* (2006.01)
*A61K 9/14* (2006.01)
*A61M 15/00* (2006.01)

(52) U.S. Cl. ............ 424/45; 424/46; 424/489; 424/434; 424/499; 514/958; 128/200.14; 128/200.24; 128/203.15

(58) Field of Classification Search .................... 424/45, 424/46, 489, 434, 499, 43; 514/958, 284, 514/165, 233.5; 128/200.14, 200.24, 203.15
See application file for complete search history.

(56) References Cited

U.S. PATENT DOCUMENTS

| | | |
|---|---|---|
| 3,219,533 A | 11/1965 | Mullins |
| 3,560,607 A | 2/1971 | Hartley et al. |
| 3,949,743 A | 4/1976 | Shanbrom |
| 3,982,095 A | 9/1976 | Robinson |
| 4,141,369 A | 2/1979 | Burruss |
| RE30,285 E | 5/1980 | Babington |
| 4,303,083 A | 12/1981 | Burruss, Jr. |
| 4,474,191 A | 10/1984 | Steiner |
| 4,484,576 A | 11/1984 | Albarda |
| 4,566,451 A | 1/1986 | Badewien |
| 4,708,151 A | 11/1987 | Shelar |
| 4,734,560 A | 3/1988 | Bowen |
| 4,735,217 A | 4/1988 | Muckenfuhs et al. |
| 4,819,665 A | 4/1989 | Roberts et al. |
| 4,848,374 A | 7/1989 | Chard et al. |
| 4,853,517 A | 8/1989 | Bowen et al. |
| 4,895,719 A | 1/1990 | Radhakrishnun et al. |
| 4,906,417 A | 3/1990 | Gentry |
| 4,917,119 A | 4/1990 | Potter et al. |
| 4,924,883 A | 5/1990 | Perfetti et al. |
| 4,941,483 A | 7/1990 | Ridings et al. |
| 4,963,289 A | 10/1990 | Ortiz et al. |
| 5,042,509 A | 8/1991 | Banerjee et al. |
| 5,049,389 A | 9/1991 | Radhakrishnun |
| 5,060,671 A | 10/1991 | Counts et al. |
| 5,099,861 A | 3/1992 | Clearman et al. |
| 5,135,009 A | 8/1992 | Muller et al. |
| 5,144,962 A | 9/1992 | Counts et al. |
| 5,146,915 A | 9/1992 | Montgomery |
| 5,224,498 A | 7/1993 | Deevi et al. |
| 5,345,951 A | 9/1994 | Serrano et al. |
| 5,366,770 A | 11/1994 | Wang |
| 5,388,574 A | 2/1995 | Ingebrethsen |
| 5,456,247 A | 10/1995 | Shilling et al. |
| 5,511,726 A | 4/1996 | Greenspan et al. |
| 5,544,646 A | 8/1996 | Lloyd et al. |
| 5,564,442 A | 10/1996 | MacDonald et al. |
| 5,592,934 A | 1/1997 | Thwaites |
| 5,605,146 A | 2/1997 | Sarela |
| 5,649,554 A | 7/1997 | Sprinkel |
| 5,666,977 A | 9/1997 | Higgins et al. |
| 5,694,919 A | 12/1997 | Rubsamen et al. |
| 5,735,263 A | 4/1998 | Rubsamen et al. |
| 5,738,865 A | 4/1998 | Baichwal et al. |
| 5,743,251 A | 4/1998 | Howell et al. |
| 5,758,637 A | 6/1998 | Ivri et al. |
| 5,819,756 A | 10/1998 | Mielordt |
| 5,840,246 A | 11/1998 | Hammons et al. |
| 5,855,913 A | 1/1999 | Hanes et al. |
| 5,874,481 A | 2/1999 | Weers et al. |

(Continued)

FOREIGN PATENT DOCUMENTS

EP 0 358 114 3/1990

(Continued)

OTHER PUBLICATIONS

Meng Yun et al.: "Pharmalogical effects of methamphetamine and other stimulants via inhalation exposure", Drug and Alcohol Dependence, vol. 52 No. 2, Jan. 7, 1999, pp. 111-120.
Office Action mailed Aug. 13, 2003 for U.S. Appl. No. 10/153,313, filed May 21, 2002 "Delivery of Benzodiazepines Through an Inhalation Route".
U.S. Appl. No. 11/621,397, filed Jan. 9, 2007, Rabinowitz et al.
U.S. Appl. No. 11/744,799, filed May 4, 2007, Hale et al.
Bennett, R. L. et al. (1981). "Patient-Controlled Analgesia: A New Concept of Postoperative Pain Relief," Annual Surg. 195(6):700-705.
Carroll, M.E. et al. (1990), "Cocaine-Base Smoking in Rhesus Monkey: Reinforcing and Physiological Effects," Psychopharmacology (Berl) 102:443-450.

(Continued)

*Primary Examiner* — Mina Haghighatian
(74) *Attorney, Agent, or Firm* — Swanson & Bratschun, L.L.C.

(57) ABSTRACT

The present invention relates to the delivery of drug amines through an inhalation route. Specifically, it relates to aerosols containing drug amines that are used in inhalation therapy. In one aspect of the present invention, a method of delivering an amine drug in an aerosol form is provided. The method comprises: a) heating a coating, which includes an amine drug salt on a substrate contained in a device to a temperature sufficient to volatilize the amine drug from the coating, b) by said heating, forming an amine drug vapor, and c) during said heating, drawing air through said device, condensing said vapor to form aerosol particles containing less than 10% degradation products of the compound.

54 Claims, 1 Drawing Sheet

U.S. PATENT DOCUMENTS

| | | |
|---|---|---|
| 5,894,841 A | 4/1999 | Voges |
| 5,915,378 A | 6/1999 | Lloyd et al. |
| 5,918,595 A | 7/1999 | Olsson |
| 5,934,272 A | 8/1999 | Lloyd et al. |
| 5,957,124 A | 9/1999 | Lloyd et al. |
| 5,960,792 A | 10/1999 | Lloyd et al. |
| 5,993,805 A | 11/1999 | Sutton et al. |
| 6,041,777 A * | 3/2000 | Faithfull et al. .......... 128/200.24 |
| 6,051,566 A | 4/2000 | Bianco |
| 6,090,212 A | 7/2000 | Mahawili |
| 6,095,134 A | 8/2000 | Sievers et al. |
| 6,102,036 A | 8/2000 | Slutsky et al. |
| 6,131,570 A | 10/2000 | Schuster et al. |
| 6,136,295 A | 10/2000 | Edwards et al. |
| 6,155,268 A | 12/2000 | Takeuchi |
| 6,158,431 A | 12/2000 | Poole |
| 6,234,167 B1 | 5/2001 | Cox et al. |
| 6,241,969 B1 | 6/2001 | Saidi et al. |
| 6,255,334 B1 | 7/2001 | Sands |
| 6,506,762 B1 | 1/2003 | Horvath et al. |
| 6,514,482 B1 * | 2/2003 | Bartus et al. .................. 424/45 |
| 6,591,839 B2 | 7/2003 | Meyer et al. |
| 6,632,047 B2 | 10/2003 | Vinegar et al. |
| 6,682,716 B2 | 1/2004 | Hodges et al. |
| 6,701,922 B2 | 3/2004 | Hindle et al. |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,772,756 B2 | 8/2004 | Shayan |
| 6,776,978 B2 | 8/2004 | Rabinowitz et al. |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 2001/0020147 A1 | 9/2001 | Staniforth et al. |
| 2002/0037828 A1 | 3/2002 | Wilson et al. |
| 2002/0058009 A1 | 5/2002 | Bartus et al. |
| 2002/0086852 A1 | 7/2002 | Cantor |
| 2002/0112723 A1 | 8/2002 | Schuster et al. |
| 2002/0117175 A1 | 8/2002 | Kottayil et al. |
| 2002/0176841 A1 | 11/2002 | Barker et al. |
| 2003/0004142 A1 | 1/2003 | Prior et al. |
| 2003/0015196 A1 | 1/2003 | Hodges et al. |
| 2003/0015197 A1 | 1/2003 | Hale et al. |
| 2003/0032638 A1 | 2/2003 | Kim et al. |
| 2003/0051728 A1 | 3/2003 | Lloyd et al. |
| 2003/0062042 A1 | 4/2003 | Wensley et al. |
| 2003/0118512 A1 | 6/2003 | Shen |
| 2003/0131843 A1 | 7/2003 | Lu |
| 2003/0138508 A1 | 7/2003 | Novack et al. |
| 2003/0209240 A1 | 11/2003 | Hale et al. |
| 2004/0016427 A1 * | 1/2004 | Byron et al. ............. 128/200.14 |
| 2004/0096402 A1 | 5/2004 | Hodges et al. |
| 2004/0099266 A1 | 5/2004 | Cross et al. |
| 2004/0099269 A1 * | 5/2004 | Hale et al. ................ 128/203.16 |
| 2004/0101481 A1 | 5/2004 | Hale et al. |
| 2004/0102434 A1 | 5/2004 | Hale et al. |
| 2004/0105818 A1 | 6/2004 | Every et al. |
| 2004/0105819 A1 | 6/2004 | Hale et al. |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0126562 A1 | 6/2005 | Rabinowitz et al. |
| 2005/0131739 A1 | 6/2005 | Rabinowitz et al. |
| 2005/0258159 A1 | 11/2005 | Hale et al. |
| 2005/0268911 A1 | 12/2005 | Cross et al. |
| 2006/0032496 A1 | 2/2006 | Hale et al. |
| 2006/0032501 A1 | 2/2006 | Hale et al. |
| 2006/0120962 A1 | 6/2006 | Rabinowitz et al. |
| 2006/0153779 A1 | 7/2006 | Rabinowitz et al. |
| 2006/0177382 A1 | 8/2006 | Rabinowitz et al. |
| 2006/0193788 A1 | 8/2006 | Hale et al. |
| 2006/0216243 A1 | 9/2006 | Rabinowitz et al. |
| 2006/0216244 A1 | 9/2006 | Rabinowitz et al. |
| 2006/0233717 A1 | 10/2006 | Hale et al. |
| 2006/0233718 A1 | 10/2006 | Rabinowitz et al. |
| 2006/0233719 A1 | 10/2006 | Rabinowitz et al. |
| 2006/0239936 A1 | 10/2006 | Rabinowitz et al. |
| 2006/0246011 A1 | 11/2006 | Rabinowitz et al. |
| 2006/0246012 A1 | 11/2006 | Rabinowitz et al. |
| 2006/0251587 A1 | 11/2006 | Rabinowitz et al. |
| 2006/0251588 A1 | 11/2006 | Rabinowitz et al. |
| 2006/0257328 A1 | 11/2006 | Rabinowitz et al. |
| 2006/0257329 A1 | 11/2006 | Rabinowitz et al. |
| 2006/0269486 A1 | 11/2006 | Rabinowitz et al. |
| 2006/0269487 A1 | 11/2006 | Rabinowitz et al. |
| 2006/0280692 A1 | 12/2006 | Rabinowitz et al. |
| 2006/0286042 A1 | 12/2006 | Rabinowitz et al. |
| 2006/0286043 A1 | 12/2006 | Rabinowitz et al. |
| 2007/0014737 A1 | 1/2007 | Rabinowitz et al. |
| 2007/0028916 A1 | 2/2007 | Hale et al. |
| 2007/0031340 A1 | 2/2007 | Hale et al. |
| 2007/0122353 A1 | 5/2007 | Hale et al. |
| 2007/0140982 A1 | 6/2007 | Every et al. |

FOREIGN PATENT DOCUMENTS

| | | |
|---|---|---|
| EP | 0 606 486 | 7/1994 |
| EP | 1 080 720 | 3/2001 |
| GB | 502 761 | 1/1938 |
| WO | WO 94/09842 | 5/1994 |
| WO | WO 96/09846 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 97/27804 | 8/1997 |
| WO | WO 97/36574 | 10/1997 |
| WO | WO 98/22170 | 5/1998 |
| WO | WO 98/31346 | 7/1998 |
| WO | WO 98/36651 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/27363 | 5/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/76673 | 12/2000 |
| WO | WO 01/05459 | 1/2001 |
| WO | WO 02/24158 | 3/2002 |
| WO | WO 02/094231 | 11/2002 |
| WO | WO 02/094232 | 11/2002 |
| WO | WO 02/098389 | 12/2002 |
| WO | WO 03/026631 | 4/2003 |
| WO | WO 03/037412 | 5/2003 |

OTHER PUBLICATIONS

Clark, A. and Byron, P. (1986). "Dependence of Pulmonary Absorption Kinetics on Aerosol Particle Size," Z. Erkrank. 166:13-24.

Darquenne, C. et al. (1997). "Aerosol Dispersion in Human Lung: Comparison Between Numerical Simulations and Experiments for Bolus Tests," American Physiological Society. 966-974.

Davies, C. N. et al. (May 1972). "Breathing of Half-Micron Aerosols," Journal of Applied Physiology. 32(5):591-600.

Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.

Finlay, W. H. (2001). "The Mechanics of Inhaled Pharmaceutical Aerosols", Academic Press: San Diego Formula 2.39. pp. 3-14 (Table of Contents). pp. v-viii.

Gonda, I. (1991). "Particle Deposition in the Human Respiratory Tract,"Chapter 176, The Lung: Scientific Foundations. Crystal R.G. and West, J.B. (eds.), Raven Publishers, New York. pp. 2289-2294.

Hatsukami D., et al. (May 1990) "A Method for Delivery of Precise Doses of Smoked Cocaine-Base to Human." Pharmacology Biochemistry & Behavior. 36(1):1-7.

Heyder, J. et al. (1986). "Deposition of Particles in the Human Respiratory Tract in the Size Range 0.005-15 µm," J. Aerosol Sci. 17(5):811-822.

Huizer, H. (1987). "Analytical Studies on Illicit Heron. V. Efficacy of Volitization During Heroin Smoking." Pharmaceutisch Weekblad Scientific Edition. 9(4):203-211.

Hurt, R. D., Md and Robertson, C. R., PhD, (Oct. 1998). "Prying Open the Door to the Tobacco Industry's Secrets About Nicotine: The Minnesota Tobacco Trial," JAMA 280(13):1173-1181.

Lichtman, A. H. et al. (1996). "Inhalation Exposure to Volatilized Opioids Produces Antinociception in Mice," Journal of Pharmacology and Experimental Therapeutics. 279(1):69-76 XP-001118649.

Martin, B. R. and Lue, L. P. (May/Jun. 1989). "Pyrolysis and Volatilization of Cocaine," Journal of Analytical Toxicology 13:158-162.

Mattox, A.J. and Carroll, M.E. (1996). "Smoked Heroin Self-Administration in Rhesus Monkeys," Psychopharmacology 125:195-201.

Meng, Y. et al. (1997). "Inhalation Studies with Drugs of Abuse", NIDA Research Monogragh 173:201-224.

Office Action mailed Dec. 4, 2003 with respect to U.S. Appl. No. 10/057,198.

Office Action mailed Dec. 15, 2003 with respect to U.S. Appl. No. 10/057,197.

Office Action mailed Jun. 3, 2004 with respect to U.S. Appl. No. 10/057,197.

Office Action mailed Jan. 12, 2005 with respect to U.S. Appl. No. 10/057,197.

Office Action mailed Feb. 27, 2004 with respect to U.S. Appl. No. 10/146,080.

Office Action mailed Aug. 25, 2005 with respect to U.S. Appl. No. 10/146,080.

Office Action mailed Jun. 5, 2006 with respect to U.S. Appl. No. 10/146,080.

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Pankow, J. (Mar. 2000). ACS Conference-San Francisco-Mar. 26, 2000. Chemistry of Tobacco Smoke. pp. 1-8.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Sekine, H. and Nakahara, Y. (1987). "Abuse of Smoking Methamphetamine Mixed with Tobacco: I. Inhalation Efficiency and Pyrolysis Products of Methamphetamine," Journal of Forensic Science 32(5): 1271-1280.

Vapotronics, Inc. (1998) located at http://www.vapotronics.com.au/banner.htm., 11 pages, (visited on Jun. 5, 2000).

Ward, M. E. Md, et al. (Dec. 1997). "Morphine Pharmacokinetics after Pulmonary Administration from a Novel Aerosol Delivery System," Clinical Pharmocology & Therapeutics 62(6):596-609.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

\* cited by examiner

DELIVERY OF DRUG AMINES THROUGH AN INHALATION ROUTE

CROSS-REFERENCE TO RELATED APPLICATIONS

This application claims priority to U.S. provisional application Ser. No. 60/380,819 entitled "Delivery of Drug Amines Through an Inhalation Route," filed May 13, 2002, Rabinowitz and Zaffaroni, the entire disclosure of which is hereby incorporated by reference.

FIELD OF THE INVENTION

The present invention relates to the delivery of drug amines through an inhalation route. Specifically, it relates to aerosols containing drug amines that are used in inhalation therapy.

BACKGROUND OF THE INVENTION

There are a number of compounds containing amines that are currently marketed as drugs. In certain circumstances, the presence of such functionality, however, can prevent effective drug delivery. This phenomenon could be due to a range of effects, including poor solubility and instability.

Inhaled drugs, however, have the potential to enter the systemic circulation and thereby circumvent a number of the problems associated with oral and other drug delivery methods. Moreover, by manipulation of particle size and/or density, delivery of drugs into the alveoli may be facilitated. Alveoli have a large surface area for drug absorption and are surrounded by an extensive capillary network which facilitates rapid passage of drugs into the pulmonary circulation. Furthermore, because blood returning from the lungs is pumped directly to the systemic arterial circulation, drugs inhaled into the alveoli have the potential to reach target organs very rapidly. Of particular importance is that drugs delivered in this manner reach their target site without being exposed to potentially degrading conditions in the gastrointestinal tract and without undergoing modification by first pass metabolism in the liver. Thus, it is desirable to provide a new route of administration for drug amines that rapidly produces peak plasma concentrations of the compounds. This invention provides a route of administration to accomplish this goal.

One type of inhalation aerosol is a condensation aerosol formed from vaporization of compounds. The use of vaporized drugs, thus, provides a method of maximizing alveolar delivery and rapidly delivering drugs to target organs. However, the heat required to vaporize a drug often also generates degradation products, which may decrease the efficacy of the thermal vapor and are undesirable to be delivered to the patient. Particularly, the salt form of a drug is expected to lower a compound's vapor pressure, and consequently raise its vaporization temperature and potentially increase the amount of degradation product that is likely generated. Thus, a method that enhances drug volatilization without the formation of a substantial amount of degradation products with amine drug salts and a method for selected amine drug salts suitable for use in condensation aerosol is needed. Therefore, one object of the invention is to provide a thermal vapor of amine drug salts for inhalation therapy that does not contain a significant amount of thermal degradation products.

Furthermore, while many drugs may be delivered in their free base form using vaporization, such as those, for example, disclosed in U.S. application Ser. No's: 10/150,591, 10/150,267, 10/155,705 and 10/152,640, some amine drugs are liquid in their free base form and thus, are not optimal in a vaporization method that uses films or coatings to generate the aerosol. In such cases, the physical or chemical stability of the coating may be enhanced through formation of the drug amine salt. Thus, another object of the present invention is to provide amine drugs with desirable properties for thermal vapor delivery.

While dry powder formulations and new liquid aerosol devices are being developed or are available for inhalation therapy. See for example, U.S. Pat. No. 5,993,805 to Sutton et al.; WO 0000176 to Robinson et al.; WO 9916419 to Tarara et al.; WO 0000215 to Bot et al.; U.S. Pat. No. 5,855,913 to Hanes et al.; and U.S. Pat. Nos. 6,136,295 and 5,874,064 to Edwards et al.; U.S. Pat. No. 6,131,570 to Schuster et al.; U.S. Pat. No. 5,724,957 to Rubsamen et al.; and U.S. Pat. No. 6,098,620 to Lloyd et al.; U.S. Pat. Nos. 5,586,550; 5,758,637; and 6,085,740 to Ivri et al.; and U.S. Pat. No. 5,938,117.

These technologies are limited, however. Dry powders require excipients to formulate the dry powders for appropriate delivery. Whereas with liquid aerosols, because the solubility of many drug compounds in water or other solvents suitable for liquid aerosol delivery is low, the total quantity of drug that can be delivered in a single breath is quite small. Thus, there is a need for condensation aerosol of amine drug salts that overcome these limitations. This invention provides such a means.

These and other features of the invention will be described in detail below. All publications, patents, and patent applications referred to herein are incorporated herein by reference in their entirety.

SUMMARY OF THE INVENTION

The present invention provides methods and reagents for selecting and generating novel amine drug condensation aerosols and vapors, as well as methods of delivering amine drug aerosols, novel thermal vapor compositions, and methods for generating therapeutically effective inhalation doses of condensation aerosols.

In one aspect, the invention provides a method for selecting amine drugs salts for use in forming a condensation aerosol comprising:
  a. dissolving or suspending a salt form of an amine drug in a solvent,
  b. coating the suspended or dissolved salt form of the amine drug on a substrate,
  c. heating the coated substrate to form a compound vapor,
  d. cooling the vapor to form aerosol particles,
  e. collecting the aerosol particles,
  f. analyzing the collected particles to determine the purity of the aerosol particles; and
  g. selecting the amine drug based on a decomposition index less than 0.15.

Other preferred embodiments are those wherein the amine drug salt is selected from the group consisting of an antibiotic, anticonvulsant, antidepressant, antiemetic, antihistamine, antiparkinsonian drug, antipsychotic, anxiolytic, drugs for erectile dysfunction, drugs for migraine headache, drugs for the treatment of addiction, muscle relaxants, non-steroidal anti-inflammatory, opioid, or analgesics.

Amine drug salts selected by the above method can be used to form novel amine drug condensations aerosols having preferably a mass median aerodynamic diameter between the range of 1 and 5, and less than 10% amine drug decomposition products. More preferable embodiments have a mass median aerodynamic diameter between the range of 1 and 3.

In another aspect of the invention, a method of delivering an amine drug in an aerosol form is provided, comprising:
 a. heating a coating, which includes an amine drug salt on a substrate contained in a device to a temperature sufficient to volatilize the amine drug from the coating,
 b. by said heating, forming a amine drug vapor, and
 c. during said heating, drawing air through said device, condensing said vapor to form aerosol particles containing less than 10% degradation products of the compound.

In more preferred embodiments of the method, the coating of the amine drug salt used has a thickness between about 0.5 and 20 μm and the aerosol particles generated have a mass median aerodynamic diameter between about 1 and 5 micrometers. More preferably, the aerosol particles generated have a mass median aerodynamic diameter of about 1 to 3 micrometers with a geometric standard deviation of about 2.5 or less.

In a third aspect of the invention, novel thermal vapors are provided. These thermal vapors comprise gas and amine drug aerosol particles,
 a. wherein said gas comprises an acid halide vapor, organic acid vapor, or organic acid decomposition product vapor, and
 b. wherein said amine drug aerosol particles
  i. comprise at least 10 micrograms of an amine drug and less than 10% amine drug decomposition products relative to said total mass of amine drug in the particles, and
  ii. have a mass median aerodynamic diameter in the range 1 to 5 micrometers.

These thermal vapors typically further contain a supersaturated amine drug vapor. Preferably such vapor is warmer than ambient temperature, and more preferably such vapor is warmer than 100° C., 200° C., 250° C., or 300° C.

In yet another aspect of the invention, a method is provided for forming a therapeutically effective inhalation does of drug amine aerosol particles with less than 10% degradation products, comprising:
 a) providing a drug delivery article comprising a body defining an interior flow-through chamber having upstream and down stream chamber ends and a drug supply unit contained within such chamber, wherein said drug supply unit comprises a heat-conductive substrate coated with a composition comprising at least a therapeutic amount of amine drug salt having a decomposition index less than 0.10;
 b) heating said heat-conductive substrate to a temperature of greater than 200° C. over a period of less than 5 seconds, thereby producing a vapor of a therapeutic dose of said amine drug salt; and
 c) flowing a gas through said chamber thereby cooling said vapor to form drug amine aerosol particles.

In the preferred embodiments, the thickness of the coating of amine drug salt on the substrate is between about 0.2 and 20 μm. The typical amine drug particle mass median aerodynamic diameter of these embodiments is between about 1 and 5 micrometers. More preferably, the amine drug particle mass median aerodynamic diameter of these embodiments is between about 1 and 3 micrometers. In a more preferred embodiment the thermal vapor consists essential of gas and amine drug aerosol particles.

DETAILED DESCRIPTION OF THE INVENTION

Figure 1:
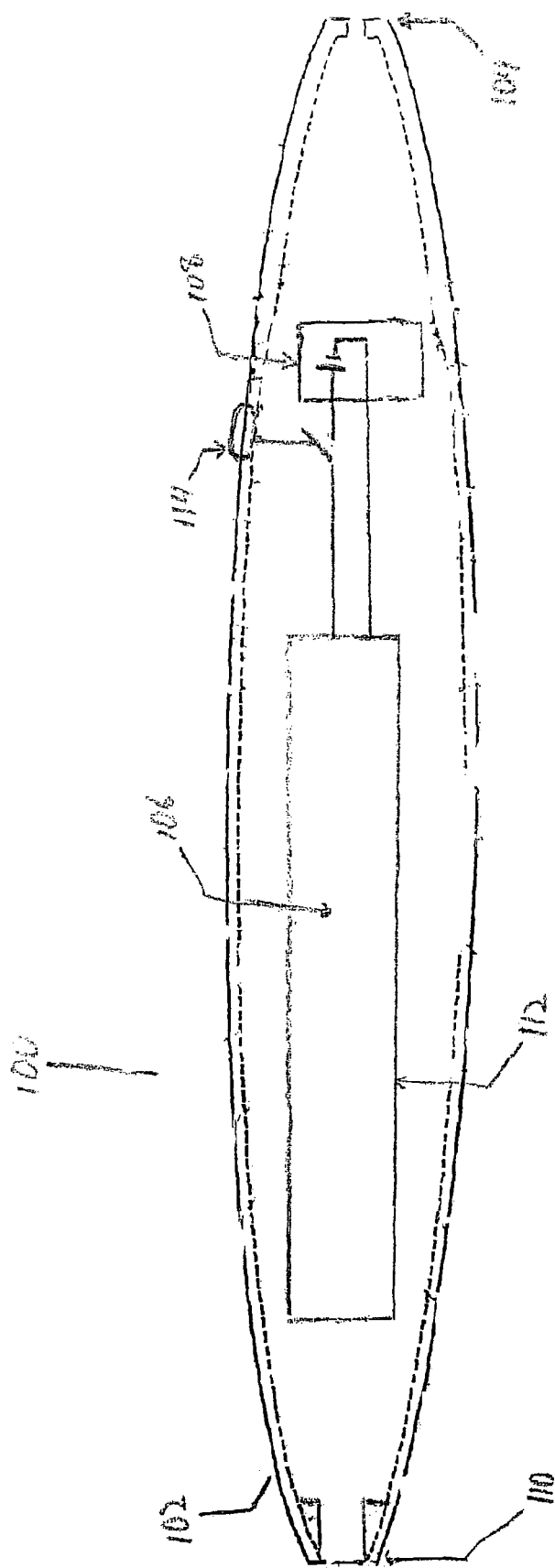
FIG. 1 is a side view showing internal details of a device for vaporizing a drug including an external chamber in accordance with the present invention for delivery of a drug to a mammal.

The present invention provides methods for screening amine drug salts for suitability in condensation aerosols; methods to deliver aerosols, novel vapor compositions, and methods to generate therapeutically effective amounts of amine aerosols. To facilitate understanding and the practice of the invention in its many and diverse applications, this description is organized as shown below.
 I. DEFINITIONS
 II. CHARACTERISTICS OF THE AMINE DRUG SALTS
 III. CHARACTERISTICS OF THE THERMAL VAPOR, AEROSOL AND/OR PARTICLES
 IV. METHODS
 V. EXAMPLES I. Definitions "Acid halide" refers to HF, HCl, HBr, HI, HAt.

"Aerodynamic diameter" of a given particle refers to the diameter of a spherical droplet with a density of 1 g/mL (the density of water) that has the same settling velocity as the given particle.

"Aerosol" refers to a suspension of solid or liquid particles in a gas.

"Aerosol drug amine mass density" refers to the mass of drug amine per unit volume of aerosol.

"Aerosol mass density" refers to the mass of particulate matter per unit volume of aerosol.

"Aerosol particle density" refers to the number of particles per unit volume of aerosol.

"Condensation aerosol" refers to an aerosol formed by vaporization of a substance followed by condensation of the substance into an aerosol.

"Decomposition index" refers to a number derived from an assay and described in Example 3 and 4. The number is determined by substracting the fractional purity of the generated aerosol from 1.

"Drug" refers to any chemical compound that is used in the prevention, diagnosis, treatment, or cure of disease, for the relief of pain, or to control or improve any physiological or pathological disorder in humans or animals. Such compounds are oftentimes listed in the Physician's Desk Reference (Medical Economics Company, Inc. at Montvale, N.J., 56$^{th}$ edition, 2002), which is herein incorporated by reference. The drugs are preferably other than recreational drugs. More specifically, the drugs are preferably other than recreational drugs used for non-medicinal recreational purposes, e.g., habitual use to solely alter one's mood, affect, state of consciousness, or to affect a body function unnecessarily, for recreational purposes. Cocaine, amphetamine, methamphetamine, and their derivatives are recreational drugs specifically excluded from the term "drug". The terms "drug" and "medication" are herein used interchangeably.

"Drug amine" refers to a drug containing a primary, secondary, or tertiary amine moiety and not a quaternary amine moiety.

"Drug amine" refers to a drug containing an amine moiety. Drug amine and "amine drug" are terms that mean the same and herein are used interchangeably.

"Drug amine salt" refers to a drug amine, where the amine group is protonated by an acid to form an ammonium salt with a corresponding counterion derived from the acid. The counterion is a pharmaceutically acceptable anion (e.g., Cl— or $CH_3CO_2$—). The drug amines from which the salts are formed come from a variety of drug classes, including, without limitation, antibiotics, anticonvulsants, antidepressants, antiemetics, antihistamines, antiparkisonian drugs, antipsychotics, anxiolytics, drugs for erectile dysfunction, drugs for migraine headaches, drugs for the treatment of alcoholism, drugs for the treatment of addiction, muscle relaxants, non-steroidal anti-inflammatories, opioids, and other analgesics. Drug amine salt and "amine drug salt" are terms that mean the same and herein are used interchangeably.

Examples of antibiotics from which drug amine salts are formed include cephalexin; cephaloglycin; cephalosporins, such as cephalosporin C; cephradine; amoxicillin; hetacillin; cyclacillin; and penicillins, such as penicillin N.

An example of anticonvulsants from which a drug amine salt is formed is tiagabine.

Examples of antidepressants from which drug amine salts are formed include amitriptyline, amoxapine, butriptyline, clomipramine, desipramine, dosulepin, doxepin, imipramine, lofepramine, medifoxamine, mianserin, mirtazapine, nortriptyline, protriptyline, trimipramine, viloxazine, citalopram, cotinine, duloxetine, fluoxetine, fluvoxamine, milnacipran, paroxetine, reboxetine, sertraline, tianeptine, iproniazid, isocarboxazid, moclobemide, phenyhydrazine, phenelzine, selegiline, sibutramine, tranylcypromine, ademetionine, amisulpride, amperozide, benactyzine, bupropion, idazoxan, metralindole, milnacipran, minaprine, nefazodone, nomifensine, ritanserin, roxindole, tofenacin, trazodone, tryptophan, and venlafaxine.

Examples of antiemetics from which drug amine salts are formed include alizapride, azasetron, benzquinamide, bromopride, buclizine, chlorpromazine, cinnarizine, clebopride, cyclizine, diphenhydramine, diphenidol, dolasetron, droperidol, granisetron, hyoscine, metoclopramide, metopimazine, ondansetron, perphenazine, promethazine, prochlorperazine, scopolamine, triethylperazine, trifluoperazine, triflupromazine, trimethobenzamide, and tropisetron.

Examples of antihistamines from which drug amine salts are formed include azatadine, brompheniramine, carbinoxamine, chlorpheniramine, clemastine, cyproheptadine, dexmedetomidine, diphenhydramine, doxylamine, hydroxyzine, cetrizine, fexofenadine, and promethazine.

Examples of antiparkisonian drugs from which drug amine salts are formed include amantadine, baclofen, biperiden, benztropine, orphenadrine, procyclidine, trihexyphenidyl, levodopa, carbidopa, selegiline, deprenyl, apomorphine, benserazide, bromocriptine, budipine, cabergoline, dihydro-ergokryptine, pramipexole, galanthamine, lazabemide, lisuride, memantine, mofegiline, pergolide, remacemide, and terguride.

Examples of antipsychotics from which drug amine salts are formed include acetophenazine, alizapride, amperozide, benperidol, benzquinamide, bromperidol, butaperazine, carphenazine, carpipramine, chlorpromazine, chlorprothixene, clocapramine, clomacran, clopenthixol, clospirazine, clothiapine, cyamemazine, droperidol, flupenthixol, fluphenazine, fluspirilene, haloperidol, mesoridazine, metofenazate, molindone, penfluridol, pericyazine, perphenazine, pimozide, pipamerone, piperacetazine, pipotiazine, prochlorperazine, promazine, remoxipride, sertindole, spiperone, sulpiride, thioridazine, thiothixene, trifluperidol, triflupromazine, trifluoperazine, ziprasidone, zotepine, zuclopenthixol, amisulpride, clozapine, melperone, olanzapine, quetiapine, and risperidone.

Examples of anxiolytics from which drug amine salts are formed include diazepam, alprazolam, triazolam, indiplon, zaleplon, mecloqualone, medetomidine, metomidate, adinazolam, chlordiazepoxide, clobenzepam, flurazepam, loprazolam, midazolam, azacyclonol, buspirone, captodiamine, enciprazine, flesinoxan, ipsapirone, lesopitron, loxapine, methaqualone, propanolol, tandospirone, trazadone, zopiclone, and zolpidem.

Examples of drugs for erectile dysfunction from which amine salts are formed include cialis (IC351), sildenafil, vardenafil, apomorphine, apomorphine diacetate, phentolamine, and yohimbine.

Examples of drugs for migraine headache from which drug amine salts are formed include almotriptan, eletriptan, alpiropride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Examples of drugs for the treatment of alcoholism from which drug amine salts are formed include naloxone and naltrexone.

An example of a drug for the treatment of addiction from which drug amine salts are formed is buprenorphine.

Examples of muscle relaxants from which drug amine salts are formed include baclofen, cyclobenzaprine, orphenadrine, quinine, and tizanidine.

Examples of nonsteroidal anti-inflammatories from which drug amine salts are formed include aceclofenac, alminoprofen, amfenac, bromfenac, carprofen, cinchophen, diclofenac, etodolac, mazipredone, meclofenamate, pirprofen, and tolfenamate.

Examples of opioids from which drug amine salts are formed include alfentanil, allylprodine, alphaprodine, anileridine, benzylmorphine, bezitramide, buprenorphine, butorphanol, cipramadol, clonitazene, codeine, dextromoramide, dextropropoxyphene, diamorphine, dihydrocodeine, diphenoxylate, dipipanone, fentanyl, hydromorphone, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Examples of other analgesics from which drug amine salts are formed include apazone, benzpiperylon, benzydramine, caffeine, clonixin, ethoheptazine, flupirtine, nefopam, orphenadrine, propacetamol, and propoxyphene.

Examples of acids used to form the drug amine salt include, without limitation, the following: hydrochloric acid; hydrobromic acid; formic acid; acetic acid; maleic acid; fumaric acid, benzoic acid, and trifluoroacetic acid.

"Drug amine degradation product" refers to a compound resulting from a chemical modification of the amine. The modification, for example, can be the result of a thermally or photochemically induced reaction. Such reactions include, without limitation, oxidation and hydrolysis.

"Inhalable aerosol drug amine mass density" refers to the aerosol drug amine mass density produced by an inhalation device and delivered into a typical patient tidal volume.

"Inhalable aerosol mass density" refers to the aerosol mass density produced by an inhalation device and delivered into a typical patient tidal volume.

"Inhalable aerosol particle density" refers to the aerosol particle density of particles of size between 100 nm and 5 microns produced by an inhalation device and delivered into a typical patient tidal volume.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Organic acid" refers to a compound, generally of less than 300 grams/mole of molecular weight, containing one or more carboxylic acid functional groups.

"Organic acid decomposition product" refers to products resulting from a chemical modification of the organic acid. The modification, for example, can be the result of a thermally or photochemically induced reaction. Such reactions include, without limitation, oxidation or decarboxylation.

"Rate of aerosol formation" refers to the mass of aerosolized particulate matter produced by an inhalation device per unit time.

"Rate of inhalable aerosol particle formation" refers to the number of particles of size between 100 nm and 5 microns produced by an inhalation device per unit time.

"Rate of drug amine aerosol formation" refers to the mass of aerosolized, drug amine produced by an inhalation device per unit time.

"Settling velocity" refers to the terminal velocity of an aerosol particle undergoing gravitational settling in air.

"Suitable drug amine salt" refers to a drug amine salt that, when subjected to the assay described in Example 2, provides a drug amine aerosol in greater than 85% purity.

"Thermal vapor" refers to a vapor phase, aerosol phase or mixture of aerosol-vapor phases, formed preferably by heating. The thermal vapor may comprise a drug and optionally a carrier, and may be formed by heating the drug and optionally a carrier.

"Treatment" refers to an approach for obtaining beneficial or desired clinical results. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

"Typical patient tidal volume" refers to 1 L for an adult patient and 15 mL/kg for a pediatric patient.

"Vapor" refers to a gas, and "vapor phase" refers to a gas phase.

II. Characteristics of The Amine Drug Salts

Preferably, the drug amine salt is a salt of a drug amine freebase, wherein the salt of the freebase has a molecular weight of greater than 200 grams/mole. More preferably, the drug amine salt has a molecular weight greater than 250 grams/mole, 300 grams/mole, or 350 grams/mole.

Preferably, the drug amine salt has a decomposition index less than 0.15. More preferably, the drug amine salt has a decomposition index less than 0.10. Most preferably, the drug amine salt has a decomposition index less than 0.05. Preferably, the composition that is heated comprises at least 10 percent by weight of drug amine salt. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of drug amine salt.

Typically, the drug amine salt is a salt of a drug amine from one of the following classes: antibiotics, anticonvulsants, antidepressants, antiemetics, antihistamines, antiparkisonian drugs, antipsychotics, anxiolytics, drugs for erectile dysfunction, drugs for migraine headaches, drugs for the treatment of alcoholism, drugs for the treatment of addiction, muscle relaxants, nonsteroidal anti-inflammatories, opioids, and other analgesics.

Typically, where the drug amine salt is a salt of an antibiotic, it is selected from a salt of one of the following compounds: cephalexin; cephaloglycin; cephalosporins, such as cephalosporin C; cephradine; amoxicillin; hetacillin; cyclacillin; and penicillins, such as penicillin N.

Typically, where the drug amine salt is a salt of an anticonvulsant, it is selected from a salt of one of the following compounds: gabapentin, tiagabine, and vigabatrin.

Typically, where the drug amine salt is a salt of an anticonvulsant, it is selected from a salt of tiagabine.

Typically, where the drug amine salt is a salt of an antidepressant, it is selected from a salt of one of the following compounds: amitriptyline, amoxapine, butriptyline, clomipramine, desipramine, dosulepin, doxepin, imipramine, lofepramine, medifoxamine, mianserin, mirtazapine, nortriptyline, protriptyline, trimipramine, viloxazine, citalopram, cotinine, duloxetine, fluoxetine, fluvoxamine, milnacipran, paroxetine, reboxetine, sertraline, tianeptine, iproniazid, isocarboxazid, moclobemide, phenyhydrazine, phenelzine, selegiline, sibutramine, tranylcypromine, ademetionine, amisulpride, amperozide, benactyzine, bupropion, idazoxan, metralindole, milnacipran, minaprine, nefazodone, nomifensine, ritanserin, roxindole, tofenacin, trazodone, tryptophan, and venlafaxine.

Typically, where the drug amine salt is a salt of an antiemetic, it is selected from a salt of one of the following compounds: alizapride, azasetron, benzquinamide, bromopride, buclizine, chlorpromazine, cinnarizine, clebopride, cyclizine, diphenhydramine, diphenidol, dolasetron, droperidol, granisetron, hyoscine, metoclopramide, metopimazine, ondansetron, perphenazine, promethazine, prochlorperazine, scopolamine, triethylperazine, trifluoperazine, triflupromazine, trimethobenzamide, and tropisetron.

Typically, where the drug amine salt is a salt of an antihistamine, it is selected from a salt of one of the following compounds: azatadine, brompheniramine, chlorpheniramine, clemastine, cyproheptadine, dexmedetomidine, diphenhydramine, doxylamine, hydroxyzine, cetrizine, fexofenadine, and promethazine.

Typically, where the drug amine salt is a salt of an antiparkisonian drug, it is selected from a salt of one of the following compounds: amantadine, baclofen, biperiden, benztropine, orphenadrine, procyclidine, trihexyphenidyl, levodopa, carbidopa, selegiline, deprenyl, apomorphine, benserazide, bromocriptine, budipine, cabergoline, dihydroergokryptine, pramipexole, galanthamine, lazabemide, lisuride, memantine, mofegiline, pergolide, remacemide, and terguride.

Typically, where the drug amine salt is a salt of an antipsychotic, it is selected from a salt of one of the following compounds: acetophenazine, alizapride, amperozide, benperidol, benzquinamide, bromperidol, butaperazine, carphenazine, carpipramine, chlorpromazine, chlorprothixene, clocapramine, clomacran, clopenthixol, clospirazine, clothiapine, cyamemazine, droperidol, flupenthixol, fluphenazine, fluspirilene, haloperidol, mesoridazine, metofenazate, molindone, penfluridol, pericyazine, perphenazine, pimozide, pipamerone, piperacetazine, pipotiazine, prochlorperazine, promazine, remoxipride, sertindole, spiperone, sulpiride, thioridazine, thiothixene, trifluperidol, triflupromazine, trifluoperazine, ziprasidone, zotepine, zuclopenthixol, amisulpride, clozapine, melperone, olanzapine, quetiapine, and risperidone.

Typically, where the drug amine salt is a salt of an anxiolytic, it is selected from a salt of one of the following compounds: diazepam, alprazolam, triazolam, indiplon, zaleplon, mecloqualone, medetomidine, metomidate, adinazolam, chlordiazepoxide, clobenzepam, flurazepam, loprazolam, midazolam, azacyclonol, buspirone, captodiamine, enciprazine, flesinoxan, ipsapirone, lesopitron, loxapine, methaqualone, propanolol, tandospirone, trazadone, zopiclone, and zolpidem.

Typically, where the drug amine salt is a salt of a drug for erectile dysfunction, it is selected from a salt of one of the following compounds: cialis (IC351), sildenafil, vardenafil, apomorphine, apomorphine diacetate, phentolamine, and yohimbine.

Typically, where the drug amine salt is a salt of a drug for migraine headache, it is selected from a salt of one of the following compounds: almotriptan, alpiropride, eletriptan, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotyline, propanolol, protriptyline, sertraline, timolol, and verapamil.

Typically, where the drug amine salt is a salt of a drug amine for the treatment of alcoholism, it is selected from a salt of one of the following compounds: naloxone, and naltrexone.

Typically, where the drug amine salt is a salt of a drug amine for the treatment of addiction it is buprenorphine.

Typically, where the drug amine salt is a salt of a muscle relaxant, it is selected from a salt of one of the following compounds: baclofen, cyclobenzaprine, orphenadrine, quinine, and tizanidine.

Typically, where the drug amine salt is a salt of a nonsteroidal anti-inflammatory, it is selected from a salt of one of the following compounds: aceclofenac, alminoprofen, amfenac, bromfenac, carprofen, cinchophen, diclofenac, etodolac, mazipredone, meclofenamate, pirprofen, and tolfenamate.

Typically, where the drug amine salt is a salt of an opioid, it is selected from a salt of one of the following compounds: alfentanil, allylprodine, alphaprodine, anileridine, benzylmorphine, bezitramide, buprenorphine, butorphanol, cipramadol, clonitazene, codeine, dextromoramide, dextropropoxyphene, diamorphine, dihydrocodeine, diphenoxylate, dipipanone, fentanyl, hydromorphone, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Typically, where the drug amine salt is a salt of an other analgesic it is selected from a salt of one of the following compounds: apazone, benzpiperylon, benzydramine, caffeine, clonixin, ethoheptazine, flupirtine, nefopam, orphenadrine, propacetamol, and propoxyphene.

Typically, where the drug amine salt is a salt of a stimulant, it is selected from a salt of one of the following compounds: amphetamine, brucine, caffeine, dexfenfluramine, dextroamphetamine, ephedrine, fenfluramine, mazindol, methylphenidate, pemoline, phentermine, and sibutramine.

Typically, the drug amine salt is a hydrochloric acid salt, hydrobromic acid salt, formic acid salt, acetic acid salt, maleic acid salt, fumaric acid salt, benzoic acid salt or trifluoroacetic acid salt.

Typically, the drug amine salt is selected from a group of salts consisting of brompheniramine maleate, carbinoxamine maleate, chlorpheniramine maleate, cyproheptadine hydrochloride, pyrilamine maleate, buproprion hydrochloride, trimipramine maleate, tranylcypromine hydrochloride, protriptyline hydrochloride, apomorphine diacetate hydrochloride, buprenorphine hydrochloride, nicotine dihydrochloride, nicotine sulfate, apomorphine hydrochloride, diphenhydramine hydrochloride, mexiletine hydrochloride, and nicotine hydrochloride..

Typically, the drug amine salt is a mono- or di-salt (e.g., monohydrochloride or dihydrochloride).

III. Characteristics of The Thermal Vapor, Aerosol and/or Particles

Typically, the particles comprise at least 5 percent by weight of drug amine. Preferably, the particles comprise at least 10 percent by weight of drug amine. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of drug amine.

Typically, the condensation aerosol particles have a mass of at least 0.01 mg. Preferably, the aerosol particles have a mass of at least 0.05 mg. More preferably, the aerosol particles have a mass of at least 0.10 mg, 0.15 mg, 0.2 g or 0.25 mg.

Typically, the particles comprise less than 10 percent by weight of drug amine degradation products relative to drug amine. Preferably, the particles comprise less than 5 percent by weight of drug amine degradation products relative to drug amine. More preferably, the particles comprise 2.5, 1, 0.5, 0.1 or 0.03 percent by weight of drug amine degradation products relative to drug amine.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, the particles of the delivered condensation aerosol have a mass median aerodynamic diameter of less than 5 microns. Preferably, the particles have a mass median aerodynamic diameter of less than 3 micrometers. More preferably, the particles have a mass median aerodynamic diameter between the range of 1-3 micrometers.

Typically, the particles of the delivered condensation aerosol have a mass median aerodynamic diameter of greater than 0.01 micrometers. Preferably, the particles have a mass median aerodynamic diameter of greater than 1 micrometers.

Typically, the geometric standard deviation around the mass median aerodynamic diameter of the aerosol particles is less than 3. Preferably, the geometric standard deviation is less than 2.5. More preferably, the geometric standard deviation is less than 2.3, 2.0, 2.0 or 1.8.

Typically, the delivered aerosol has an inhalable aerosol drug mass density of between 0.1 mg/L and 100 mg/L. Preferably, the aerosol has an inhalable aerosol drug mass density of between 0.1 mg/L and 75 mg/L. More preferably, the aerosol has an inhalable aerosol drug mass density of between 0.1 mg/L and 50 mg/L.

Typically, the delivered aerosol has an inhalable aerosol particle density greater than $10^6$ particles/mL. Preferably, the aerosol has an inhalable aerosol particle density greater than $10^7$ particles/mL or $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered condensation aerosol is formed at a rate greater than 0.5 mg/second. Preferably, the aerosol is formed at a rate greater than 0.75 mg/second. More preferably, the aerosol is formed at a rate greater than 1 mg/second, 1.5 mg/second or 2 mg/second.

Typically, the thermal vapor comprises a gas and amine drug aerosol particles,
 a. wherein said gas comprises an acid halide vapor, organic acid vapor, or organic acid decomposition product vapor, and
 b. wherein said amine drug aerosol particles
  i. comprise at least 10 micrograms of an amine drug and less than 10% amine drug decomposition products relative to said total mass of amine drug in the particles, and
  ii. have a mass median aerodynamic diameter in the range 1 to 5 micrometers.

Typically, the thermal vapor also includes supersaturated amine drug vapor. Generally, the supersaturated amine drug vapor is at a temperature greater than 200° C. More preferably, the temperature of the supersaturated amine drug vapor is greater than 300° C.

Preferably, the composition that is heated comprises at least 10 percent by weight of drug amine salt. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of drug amine salt.

A number of gases can be used in the invention, including but not limited to air, nitrogen, argon, and carbon dioxide. The preferred embodiment includes air as a gas.

Typically, between 0.1 mg and 100 mg of drug amine are delivered to the mammal in a single inspiration. Preferably, between 0.1 mg and 75 mg of drug amine are delivered to the mammal in a single inspiration. More preferably, between 0.1 mg and 50 mg of drug amine are delivered in a single inspiration.

Typically, the delivered condensation aerosol results in a peak plasma concentration of drug amine in the mammal in less than 1 h. Preferably, the peak plasma concentration is reached in less than 0.5 h. More preferably, the peak plasma concentration is reached in less than 0.2, 0.1, 0.05, 0.02 or 0.01 h.

IV. Methods

Selection of Drug Amine Salts for Condensation Aerosols

In one aspect the present invention provides a method of selecting an amine drug salt suitable for use in forming a condensation aerosol, comprising
 a. dissolving or suspending an amine drug salt in a solvent,
 b. coating the suspended or dissolved amine drug salt on a substrate,
 c. heating the coated substrate to form a compound vapor,
 d. cooling the vapor to form aerosol particles,
 e. collecting the aerosol particles,
 f. analyzing the collected particles to determine the purity of the aerosol particles; and
 g, selecting the amine drug based on a decomposition index less than 0.15.

Substrates on which the composition is heated are of a variety of shapes. Examples of such shapes include, without limitation, cylinders of less than 1.0 mm in diameter, boxes of less than 1.0 mm thickness and virtually any shape permeated by small (e.g., less than 1.0 mm-sized) pores. Preferably, substrates provide a large surface to volume ratio (e.g., greater than 100 per meter) and a large surface to mass ratio (e.g., greater than 1 cm$^2$ per gram).

A substrate of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials are used to construct the substrates. Classes of such materials include, without limitation, metals, inorganic materials, and polymers. The following are examples of the material classes: aluminum, silver, gold, stainless steel, copper and tungsten; silica, glass, silicon and alumina; graphite; polytetrafluoroethylene and polyethylene glycol. Combinations of materials and coated variants of materials are used as well.

Where aluminum is used as a solid support, aluminum foil is a suitable material. Examples of silica, alumina and silicon based materials include amphorous silica S-5631 (Sigma, St. Louis, Mo.), BCR171 (an alumina of defined surface area greater than 2 m$^2$/g from Aldrich, St. Louis, Mo.) and a silicon wafer as used in the semiconductor industry. Chromatography resins such as octadecyl silane chemically bonded to porous silica are exemplary coated variants of silica.

In a preferred embodiment of the invention, the substrate is metallic. In more preferred embodiments, the substrate is aluminum foil or stainless steel.

The heating of the drug amine salt compositions is performed using any suitable method. Examples of methods by which heat can be generated include the following: passage of current through an electrical resistance element; absorption of electromagnetic radiation, such as microwave or laser light; and, exothermic chemical reactions, such as exothermic solvation, hydration of pyrophoric materials, oxidation of combustible materials and heating on a hot plate.

The substrate is typically heated to a temperature of at least 200° C. to vaporize the amine drug salt. In more preferred embodiments, the substrate is heated to at least 300° C., 350° C., or 400° C.

The particles are collected by means known to those of skill in the art; preferred means include collection in a vial or on a filter.

The resultant particles are analyzed by any technique known by those of skill in the art., including those disclosed below under Analysis of Drug Amine Aerosols. Preferred methods of analyses include reverse-phase HPLC by absorption of UV light, typically at 225 nm and LC/MS.

A drug amine salt was preferred for aerosolization where the purity of the drug isolated by this method was greater than 85%. Such a drug amine salt has a decomposition index less than 0.15. The decomposition index was arrived at by substracting the fractional purity (i.e., 0.85) from 1.

Formation and Delivery of Drug Amine Containing Aerosols

Any suitable vaporization method is used to form the aerosols of the present invention. A preferred method, however, involves heating a thin coating or film of a composition comprising a drug amine salt to form a vapor, followed by cooling of the vapor such that it condenses to provide a drug amine comprising aerosol (condensation aerosol). The composition is heated in one of two forms: as pure active compound (i.e., pure drug amine salt); or, as a mixture of active compound and a pharmaceutically acceptable excipient.

Typically, upon heating of the composition, in addition to vaporizing the drug amine, the acidic component of the salt or a decomposition product thereof is also vaporized. For example, upon heating of a salt of a drug amine and an acid, wherein there is an equilibrium between the cationic drug amine plus the anionic acid and the neutral form of the drug amine plus the neutral acid, the acid may vaporize leaving behind the freebase (neutral form) of the drug amine which subsequently vaporizes. Such vaporization may occur at a greater rate if the equilibrium results in a comparatively larger amount of the neutral form of the drug amine and acid, and if the neutral form of the acid has a high vapor pressure (e.g., HCl). As such, in a preferred embodiment of the invention, the acid component of the drug salt is selected to favor such an equilibrium, or is selected for its high vapor pressure. In cases where the acid component of the drug amine salt is an organic acid, an alternative series of events may occur, which involves decarboxylation of the organic acid to form carbon dioxide plus organic acid decomposition products. Such decarboxylation may leave behind the drug amine in its freebase (neutral) form which may subsequently vaporize. In the case where the organic acid is, for example, lactic or tartaric acid or pyruvic acid, the acid may decompose to generate acetaldehyde in addition to carbon dioxide. In preferred embodiments of the invention the counterion degrades to form carbon dioxide. In other preferred embodiments, the counterion boils at less than 50° C., less than 100° C., or less than 200° C.

In a particularly preferred embodiment, an amine drug aerosol is formed and delivered by a method, comprising:
  a. heating a coating, which includes an amine drug salt on a substrate contained in a device to a temperature sufficient to volatilize the amine drug from the coating,
  b. by said heating, forming a amine drug vapor, and
  c. during said heating, drawing air through said device, condensing said vapor to form aerosol particles containing less than 10% degradation products of the compound.

To deliver a compound through the thermal aerosol route without significant thermal decomposition prior to vaporizing, a key component of the invention involves the use of a coating of the drug as a thin film prior to vaporizing it. Such thin film coatings generally result in vaporization of drug salt amines without substantial decomposition, with thinner coatings generally resulting in less decomposition than thicker coatings. In general, coatings in the range of thickness from 0.05 to 50 micrometers are preferred, with coatings in the range of thickness of 0.1 to 30 micrometers more preferred, and 0.2 to 20 micrometers most preferred. Coatings at the thinner end of the ranges are preferred for drug amines with a substantial tendency to decompose upon heating, whereas the thicker coatings can be employed for drug amines with less tendency to decompose upon heating.

In addition, certain drug amines may undergo decomposition reactions that occur substantially more rapidly in the liquid phase than in the solid phase. For such drug amines, it is particularly preferred to form amine drug salts that sublime upon heating. In a preferred embodiment of the invention, the drug salt amine sublimes at greater than 0.001 atm, 0.01 atm, 0.1 atm, or 1 atm of pressure.

Preferably, the drug amine salt used in the methods of the invention has a decomposition index less than 0.10. More preferably, the drug amine salt has a decomposition index less than 0.05. Preferably, the composition that is heated comprises at least 10 percent by weight of drug amine salt. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of drug amine salt.

Pharmaceutically acceptable excipients that are volatile or nonvolatile may be included in compositions of the methods. Volatile excipients, when heated, are concurrently volatilized, aerosolized and inhaled with drug amine. Classes of such excipients are known in the art and include, without limitation, gaseous, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax;; and mixtures thereof.

Substrates on which the composition is heated are of a variety of shapes. Examples of such shapes include, without limitation, cylinders of less than 1.0 mm in diameter, boxes of less than 1.0 mm thickness and virtually any shape permeated by small (e.g., less than 1.0 mm-sized) pores. Preferably, substrates provide a large surface to volume ratio (e.g., greater than 100 per meter) and a large surface to mass ratio (e.g., greater than 1 $cm^2$ per gram).

A substrate of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials are used to construct the substrates. Classes of such materials include, without limitation, metals, inorganic materials, carbonaceous materials and polymers. The following are examples of the material classes: aluminum, silver, gold, stainless steel, copper and tungsten; silica, glass, silicon and alumina; graphite; polytetrafluoroethylene and polyethylene glycol. Combinations of materials and coated variants of materials are used as well.

Where aluminum is used as a solid support, aluminum foil is a suitable material. Examples of silica, alumina and silicon based materials include amphorous silica S-5631 (Sigma, St. Louis, Mo.), BCR171 (an alumina of defined surface area greater than 2 $m^2/g$ from Aldrich, St. Louis, Mo.) and a silicon wafer as used in the semiconductor industry. Chromatography resins such as octadecyl silane chemically bonded to porous silica are exemplary coated variants of silica.

The heating of the drug amine salt compositions is performed using any suitable method. Examples of methods by which heat can be generated include the following: passage of current through an electrical resistance element; absorption of electromagnetic radiation, such as microwave or laser light; and, exothermic chemical reactions, such as exothermic solvation, hydration of pyrophoric materials and oxidation of combustible materials.

Drug amine containing aerosols of the present invention are delivered using an inhalation device. Where the aerosol is a condensation aerosol, the device has at least three elements: an element for heating a drug amine salt containing composition to form a vapor; an element allowing the vapor to cool, thereby providing a condensation aerosol; and, an element permitting inhalation of the aerosol. Various suitable heating methods are described above. The element that allows cooling is, in it simplest form, an inert passageway linking the heating means to the inhalation means. The element permitting inhalation is an aerosol exit portal that forms a connection between the cooling element and the mammal's respiratory system.

One device used to deliver the drug amine containing aerosol is described in reference to FIG. 1. Delivery device 100 has a down stream chamber end 102 and a upstream chamber end 104, a drug supply unit 106, a power source 108, and a mouthpiece 110.

A drug amine salt composition is deposited on a surface 112 of the drug supply unit 106. Upon activation of a user activated switch 114, power source 108 initiates heating of the drug supply unit 106 (e.g., through ignition of combustible fuel or passage of current through a resistive heating element). The drug amine composition volatilizes due to the heating of the drug supply unit 106 and condenses to form a condensation aerosol prior to reaching the mouthpiece 110 at the downstream chamber end of the device 102. Air flow traveling from the device upstream chamber end 104 to the mouthpiece 110 carries the condensation aerosol to the mouthpiece 110, where it is inhaled.

Devices, if desired, contain a variety of components to facilitate the delivery of drug amine containing aerosols. For instance, the device may include any component known in the art to control the timing of drug aerosolization relative to inhalation (e.g., breath-actuation), to provide feedback to patients on the rate and/or volume of inhalation, to prevent excessive use (i.e., "lock-out" feature), to prevent use by unauthorized individuals, and/or to record dosing histories.

Dosage of Drug Amine Containing Aerosols

A typical dosage of a drug amine aerosol is either administered as a single inhalation or as a series of inhalations taken within an hour or less (dosage equals sum of inhaled amounts). Where the drug amine is administered as a series of inhalations, a different amount may be delivered in each inhalation. The dosage amount of drug amine in aerosol form is generally no greater than twice the standard dose of the drug amine given orally.

One can determine the appropriate dose of drug amine containing aerosols to treat a particular condition using methods such as animal experiments and a dose-finding (Phase I/II) clinical trial. One animal experiment involves measuring plasma concentrations of drug amine in an animal after its exposure to the aerosol. Mammals such as dogs or primates are typically used in such studies, since their respiratory systems are similar to that of a human. Initial dose levels for testing in humans is generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered.

In another aspect of the invention, a method is provided for forming an effective human therapeutic inhalation dose of drug amine aerosol particles having less than 10% degradation products and a drug amine particle mass median aerodynamic diameter between about 1 and 5 micrometers, comprising:
  a) providing a drug delivery article comprising a body defining an interior flow-through chamber having upstream and down stream chamber ends and a drug supply unit contained within such chamber, wherein said drug supply unit comprises a heat-conductive substrate coated with a composition comprising at least a therapeutic amount of amine drug salt having a decomposition index less than 0.10;
  b) heating said heat-conductive substrate to a temperature of greater than 200° C. over a period of less than 5 seconds, thereby producing a vapor of a therapeutic dose of said amine drug salt; and
  c) flowing a gas through said chamber thereby cooling said vapor to form drug amine aerosol particles A number of drug delivery devices can be used including the one describe in FIG. 1 and above.

Preferably, the drug amine salt used in the method of the invention has a decomposition index less than 0.10. More preferably, the drug amine salt has a decomposition index less than 0.05. Preferably, the composition that is heated comprises at least 10 percent by weight of drug amine salt. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of drug amine salt.

The preferred coatings are those that result in vaporization of drug salt amines without substantial decomposition and are in the range of thickness from 0.05 to 50 micrometers. More preferred coatings are in the range of thickness of 0.1 to 30 micrometers, and the most preferred thickness is in the range 0.2 to 20 micrometers.

Analysis of Drug Amine Containing Aerosols

Purity of a drug amine containing aerosol is determined using a number of methods, examples of which are described in Sekine et al., *Journal of Forensic Science* 32:1271-1280 (1987) and Martin et al., *Journal of Analytic Toxicology* 13:158-162 (1989). One method involves forming the aerosol in a device through which a gas flow (e.g., air flow) is maintained, generally at a rate between 0.4 and 60 L/min. The gas flow carries the aerosol into one or more traps. After isolation from the trap, the aerosol is subjected to an analytical technique, such as gas or liquid chromatography, that permits a determination of composition purity.

A variety of different traps are used for aerosol collection. The following list contains examples of such traps: filters; glass wool; impingers; solvent traps, such as dry ice-cooled ethanol, methanol, acetone and dichloromethane traps at various pH values; syringes that sample the aerosol; empty, low-pressure (e.g., vacuum) containers into which the aerosol is drawn; and, empty containers that fully surround and enclose the aerosol generating device. Where a solid such as glass wool is used, it is typically extracted with a solvent such as ethanol. The solvent extract is subjected to analysis rather than the solid (i.e., glass wool) itself. Where a syringe or container is used, the container is similarly extracted with a solvent.

The gas or liquid chromatograph discussed above contains a detection system (i.e., detector). Such detection systems are well known in the art and include, for example, flame ionization, photon absorption and mass spectrometry detectors. An advantage of a mass spectrometry detector is that it can be used to determine the structure of drug amine degradation products.

Particle size distribution of a drug amine containing aerosol is determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density is determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the tidal volume of an inhaling patient.

Inhalable aerosol drug amine mass density is determined, for example, by delivering a drug amine-containing aerosol into a confined chamber via an inhalation device and measuring the amount of non-degraded drug collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of non-degraded drug amine collected in the chamber is determined by extracting the chamber, conducting chromatographic analysis of the extract and comparing the results of the chromatographic analysis to those of a standard containing known amounts of drug amine.

Inhalable aerosol particle density is determined, for example, by delivering aerosol phase drug amine into a confined chamber via an inhalation device and measuring the number of particles of given size collected in the chamber. The number of particles of a given size may be directly measured based on the light-scattering properties of the particles. Alternatively, the number of particles of a given size is determined by measuring the mass of particles within the given size range and calculating the number of particles based on the mass as follows: Total number of particles=Sum (from size range 1 to size range N) of number of particles in each size range. Number of particles in a given size range = Mass in the size range/Mass of a typical particle in the size range. Mass of a typical particle in a given size range=$\pi *D^3 * \phi/6$, where D is a typical particle diameter in the size range (generally, the mean boundary MMADs defining the size range) in microns, $\phi$ is the particle density (in g/mL) and mass is given in units of picograms ($g^{-12}$).

Rate of inhalable aerosol particle formation is determined, for example, by delivering aerosol phase drug amine into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation is determined, for example, by delivering aerosol phase drug amine into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug amine aerosol formation is determined, for example, by delivering a drug amine containing aerosol into a confined chamber via an inhalation device over a set period of time (e.g., 3 s). Where the aerosol is pure drug amine, the amount of drug collected in the chamber is measured as described above. The rate of drug amine aerosol formation is equal to the amount of drug ester aerosol collected in the chamber divided by the duration of the collection time. Where the drug amine containing aerosol comprises a pharmaceutically acceptable excipient, multiplying the rate of aerosol formation by the percentage of drug ester in the aerosol provides the rate of drug aerosol formation.

The drug amine containing aerosols of the present invention are typically used for the same indication for which they are given orally. For instance, baclofen would be used to treat parkinsons disease and fexofenadine would be used to treat allergy symptoms.

As will be apparent to those of skill in the art upon reading of this disclosure, the present invention provides valuable methods relating to amine drug aerosols. The above description of necessity provides a limited and merely illustrative sampling of the specific compounds, substrates, and devices features and should not be construed as limiting the scope of the invention. Other features and advantages of the invention will be apparent from the following examples and claims.

EXAMPLES

The following examples describe specific aspects of the invention to illustrate the invention and also provide a description of the methods used to select amine base salts suitable for forming condensation aerosols, and methods to generate amine drug aerosols and measure various physical properties of such aerosols to aid those of skill in the art in understanding and practicing the invention. The examples should not be construed as limiting the invention, in any manner.

Drug amine salts are typically commercially available from Sigma (www.sigma-aldrich.com), obtained in tablet form from a pharmacy and extracted, or synthesized using well known methods in the art.

Example 1

General Procedure A for Volatilizing Drug Amines from Drug Amine Salts

General Procedure for the Preparation of a Coating Solution

The concentration of a solution for coating of the substrate was typically 50-200 mg/ml. The amine drug salt was dissolved in an appropriate solvent. Common solvent choices included methanol, dichloromethane, and a 3:1 chloroform:methanol mixture, although DMF was used for less soluble amine drug salts and deionized water was used for amine drug salts that were insoluble in organic solvents. Occasionally sonication or heat was necessary to dissolve the compound.

Volatilization

A solution of drug amine salt in a minimal amount of solvent was typically coated on a piece of aluminum foil (precleaned with acetone). The solvent was allowed to evaporate. The coated foil was wrapped around a 300 watt halogen tube (Feit Electric Company, Pico Rivera, Calif.), which was inserted into a glass tube sealed at one end with a rubber stopper. Running 60 V of alternating current (driven by line power controlled by a variac) through the bulb for 5-15 s or 90 V for 3.5-5 s afforded a thermal vapor (including aerosol), which was collected on the glass tube walls. (When desired, the system was flushed through with argon prior to volatilization.) Reverse-phase HPLC analysis with detection by absorption of UV light, generally at 225 nm, was used to determine the purity of the aerosol.

Example 2

General Procedure B for Volatilizing Drug Amines from Drug Amine Salts

Dip Coating

The substrate, consisting of a hollow stainless steel cylinder with thin walls, typically having a wall thickness of 0.12 mm, diameter 13 mm, and length 36 mm and conducive to resistance heating, was dip-coated with an amine drug salt coating solution (prepared as disclosed in Example 1) typically using a computerized dip-coating machine to produce a thin layer of drug on the outside of the substrate surface. Prior to using, the substrates were cleaned in dichloromethane, methanol, and acetone, then dried, and fired at least once to remove any residual volatile material. The substrate was lowered into the drug solution and then removed from the solvent at a rate of typically 5-25cm/sec. The substrate was then allowed to dry for 30 minutes inside a fume hood. If either DMF or a water mixture was used as a dip coating solvent, the substrate was vacuum dried inside a desiccator for a minimum of one hour. Once the substrate was solvent free and only the drug remained, it was ready for volatilization. The drug-coated portion of the cylinder generally has a surface area of 8.5 cm$^2$. By assuming a unit density for the drug, the initial drug coating thickness were calculated.

Volatilization

A dip coated substrate was placed in a surrounding glass tube connected at the exit end via Tygon tubing to a filter holder fitted with a Savillex Teflon filter and the junction is sealed with paraffin film. The substrate was placed in a fitting which connects it to two 1 farad capacitors wired in series and controlled by a 12-volt relay. The capacitors were charged by a separate power source to about 16-21 volts and all the power was channeled to the substrate by closing a switch and allowing the capacitors to discharge into the substrate. The substrate was heated to a temperature of ~400° C. in ~50 milliseconds. This heating process was done under an airflow of 15 L/min, which swept the vaporized drug aerosol into a 2 micron Teflon filter. After volatilization, the aerosol captured on the filter was recovered for analysis. Any material deposited on the glass sleeve or remaining on the substrate was also recovered. The recovered materials were analyzed by HPLC UV absorbance, generally at 225 nm, or alternatively at 250, 275, or 280 nm, using a gradient method aimed at detection of impurities. The samples were further analyzed by LC/MS to confirm the molecular weight of the drug and any degradants.

Table 1, which follows, provides data from drug amines volatilized using the above-recited general procedures A and B.

TABLE 1

| Generic Name | MW | Dose (mg) | Method | Surface Area | Thickness (μm) | Mass coated (mg) | Yield | % Purity |
|---|---|---|---|---|---|---|---|---|
| Apomorphine HCl | 304 | 2 | B | 6 | 1.1 | 0.68 | 0.60 | 98.1 |
| Apomorphine HCl Diacetate | 388 | 2 | A | 20 | 1.0 | 1.9 | 1.65 | 94 |
| Brompheniramine Maleate | 435 | 2 | A | 20 | 2.8 | 5.60 | 3.4 | 99.6 |
| Brompheniramine Maleate | 435 | 2 | A under argon | 20 | 3.2 | 6.40 | 3.2 | 100 |
| Buprenorphine HCl | 504 | 0.3 | A | 20 | 1.1 | 2.10 | 1.37 | 91.4 |
| Buprenorphine HCl | 504 | 0.3 | A | 20 | 0.05 | 0.1 | 0.08 | 98.0 |
| Bupropion HCl | 276 | 100 | A | 20 | 1.1 | 2.30 | 2.1 | 98.5 |
| Bupropion HCl | 276 | 100 | A under argon | 20 | 1.1 | 2.30 | 1.8 | 99.1 |
| Buspirone HCl | 422 | 15 | A | 20 | 4.2 | 8.30 | 2.42 | 97.8 |
| Carbinoxamine Maleate | 407 | 4 | A | 20 | 3.9 | 7.70 | 4.8 | 99 |
| Carbinoxamine Maleate | 407 | 4 | A under argon | 20 | 3.4 | 6.8 | 3.0 | 100 |
| Chlorpheniramine Maleate | 391 | 8 | A | 20 | 1.6 | 3.20 | 2.1 | 99.6 |
| Chlorpheniramine Maleate | 391 | 8 | A under argon | 20 | 2.1 | 4.2 | 2.1 | 100 |
| Clemastine Fumarate | 460 | 1.34 | A | 20 | 2.9 | 5.70 | 1.8 | 76.6 |
| Cyproheptadine HCl | 324 | 4 | A | 20 | 2.2 | 4.30 | 2.6 | 99.6 |
| Cyproheptadine HCl | 324 | 4 | A under argon | 20 | 1.8 | 3.5 | 2.1 | 99.6 |
| Diphenhydramine HCl | 292 | 25 | A | 20 | 2.5 | 4.9 | 3.7 | 90.3 |
| Diphenhydramine HCl | 292 | 25 | A under argon | 20 | 2.6 | 5.2 | 3.9 | 93.3 |
| Enalapril maleate | 493 | 5 | B | 8 | 1.1 | 0.85 | 0.29 | 61.0 |

TABLE 1-continued

| Generic Name | MW | Dose (mg) | Method | Surface Area | Thickness (μm) | Mass coated (mg) | Yield | % Purity |
|---|---|---|---|---|---|---|---|---|
| Fluphenazine 2HCl | 510 | 1 | B | 8 | 1.0 | 0.78 | 0.33 | 80.7 |
| Hydroxyzine 2HCl | 448 | 50 | A | 20 | 13.7 | 27.30 | 0.25 | 41.2 |
| Hydroxyzine 2HCl | 448 | 50 | A under argon | 20 | 12.8 | 25.60 | 1.4 | 70.8 |
| Meclizine 2HCl | 464 | 25 | A | 20 | 9.7 | 19.40 | 0.5 | 75.3 |
| Meclizine 2HCl | 464 | 25 | A under argon | 20 | 11.7 | 23.40 | 0.4 | 70.9 |
| Mexiletine HCl | 216 | 200 | B | 8 | 0.9 | 0.75 | 0.44 | 99.4 |
| Nicotine HCl | 198 | 1 | A | 32 | 3.2 | 10.3 | 5.4 | 99.9 |
| Nicotine 2HCl | 235 | 1 | A | 32 | 4.6 | 14.8 | 12.9 | 99.5 |
| Nicotine Sulfate | 260 | 1 | A | 32 | 2.5 | 8.0 | 1.8 | 97.0 |
| Prochlorperazine 2HCl | 446 | 5 | B | 8 | 0.8 | 0.65 | 0.24 | 72.4 |
| Protriptyline HCl | 299 | 15 | A | 20 | 1.1 | 2.20 | 0.99 | 99.7 |
| Protriptyline HCl | 299 | 15 | A under argon | 20 | 1.1 | 2.1 | 1.1 | 99.8 |
| Pyrilamine Maleate | 401 | 25 | A | 20 | 10.8 | 21.50 | 10.5 | 93.7 |
| Pyrilamine Maleate | 401 | 25 | A under argon | 20 | 10.2 | 20.4 | 9.6 | 90.7 |
| Tranylcypromine HCl | 169 | 30 | A | 20 | 1.2 | 2.30 | 1.3 | 97.5 |
| Tranylcypromine HCl | 169 | 30 | A under argon | 20 | 1.0 | 2.0 | 1.2 | 97.2 |
| Trifluoperazine 2HCl | 480 | 7.5 | B | 8 | 1.2 | 0.97 | 0.52 | 87.5 |
| Trimipramine Maleate | 411 | 50 | A | 20 | 1.2 | 2.40 | 1.6 | 95.9 |
| Trimipramine Maleate | 411 | 50 | A under argon | 20 | 1.1 | 2.20 | 2.1 | 97.4 |

Example 3

General Procedure A for Screening Drug Amine Salts for Aerosolization Preferability Drug amine salt (1 mg) was dissolved or suspended in a minimal amount of solvent, such as for example, methanol. The solution or suspension was pipeted onto the middle portion of a 3 cm by 3 cm piece of aluminum foil. The coated foil was wrapped around the end of a 1½ cm diameter vial and secured with parafilm. A hot plate was preheated to approximately 300° C., and the vial was placed on it foil side down. The vial was left on the hotplate for 10 s after volatilization or decomposition had begun. After removal from the hotplate, the vial was allowed to cool to room temperature. The foil was removed, and the vial was extracted with dichloromethane followed by saturated aqueous NaHCO₃. The organic and aqueous extracts were shaken together, separated, and the organic extract is dried over Na₂SO₄. An aliquot of the organic solution was removed and injected into a reverse-phase HPLC with detection by absorption of UV light, generally at 225 nm. A drug amine salt was preferred for aerosolization where the purity of the drug isolated by this method was greater than 85%. Such a drug amine salt has a decomposition index less than 0.15. The decomposition index was arrived at by substracting the fractional purity (i.e., 0.85) from 1.

Example 4

General Procedure B for Screening Drug Amine Salts for Aerosolization Preferability Volatilizations were done using a setup which consists of two 1 farad capacitors wired in series and controlled by a 12-volt relay. A dip coated substrate (prepared as described in Example 2) was placed in a surrounding tube connected at the exit end via Tygon tubing to a filter holder fitted with a Savillex Teflon filter and the junction is sealed with paraffin film. The substrate was placed in a fitting which connects it to the capacitors. The capacitors were charged by a separate power source to about 16-21 volts and all the power was channeled to the substrate by closing a switch and allowing the capacitors to discharge into the substrate. The substrate was heated to a temperature of ~400° C. in ~50 milliseconds. This heating process was done under an airflow of 15 L/min, which swept the vaporized drug aerosol into a 2 micron Teflon filter. After volatilization, the aerosol captured on the filter was recovered for analysis. Any material deposited on the glass sleeve or remaining on the substrate was also recovered. The recovered materials were analyzed by HPLC UV absorbance, generally at 225 nm, or alternatively at 250, 275, or 280 nm, using a gradient method aimed at detection of impurities. The samples were further analyzed by LC/MS to confirm the molecular weight of the drug and any degradants. A drug amine salt was preferred for aerosolization where the purity of the drug isolated by this method was greater than 85%. Such a drug amine salt has a decomposition index less than 0.15. The decomposition index was arrived at by substracting the fractional purity (i.e., 0.85) from 1.

Example 5

Particle Size, Particle Density, and

Rate of Inhalable Particle Formation of Amine Drug Aerosol

A solution of 50-200 mg of amine drug salt per mL of solvent was spread out in a thin layer on the central portion of a 3.5 cm×7 cm sheet of aluminum foil. The solvent was allowed to evaporate. The aluminum foil was wrapped around a 300 watt halogen tube, which was inserted into a T-shaped glass tube. Both of the openings of the tube were sealed with parafilm, which was punctured with fifteen needles for air flow. The third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within 1 s, an aerosol appeared and was drawn into the 1 L flask by use of the piston, with collection of the aerosol terminated after 3.5-6 s. The aerosol was analyzed by connecting the 1 L flask to an eight-stage Andersen non-viable cascade impactor. MMAD of the collected aerosol ranged between 1 and 3 microns with a geometric standard deviation of less than 3. The number of particles collected on the various stages of the cascade impactor was given by the mass collected on the stage divided by the mass of a typical particle trapped on that stage. The mass of a single particle of diameter D is given by the volume of the particle, $\pi D^3/6$, multiplied by the density of the drug (taken to be 1 g/cm$^3$). The inhalable aerosol particle density is the sum of the numbers of particles collected on impactor stages 3 to 8 divided by the collection volume of 1 L. The rate of inhalable aerosol particle formation is the sum of the numbers of particles collected on impactor stages 3 through 8 divided by the formation time.

Example 6

Drug Mass Density of Amine Drug Aerosol From Amine Drug Salts

A solution of 50-200 mg of amine drug salt per mL of solvent was spread out in a thin layer on the central portion of a 3.5 cm×7 cm sheet of aluminum foil. The solvent was allowed to evaporate. The aluminum foil was wrapped around a 300 watt halogen tube, which was inserted into a T-shaped glass tube. Both of the openings of the tube were sealed with parafilm, which was punctured with fifteen needles for air flow. The third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within seconds, an aerosol appeared and was drawn into the 1 L flask by use of the piston, with formation of the aerosol terminated after about 3.5-5 s. The aerosol was allowed to sediment onto the walls of the 1 L flask for approximately 30 minutes. The flask was then extracted with acetonitrile and the extract analyzed by HPLC with detection by light absorption at 225 nm. Comparison with standards containing known amounts of the amine drug revealed the purity of the amine drug that had been collected in the flask, resulting in a calculatable aerosol drug mass density.

Although certain embodiments and examples have been used to describe the present invention, it will be apparent to those of skill in the art that changes may be made to those described embodiments and examples without departing from the scope or spirit of the invention of the following claims.

What is claimed:

1. A condensation aerosol for delivery of a drug amine formed by heating a coating of a composition comprising a salt of the drug amine on a substrate, to produce a vapor, and cooling the vapor to form a condensation aerosol comprising particles,
   wherein the particles comprise at least 10 percent by weight of the drug amine and less than 10 percent by weight of drug amine degradation products,
   wherein the condensation aerosol has a mass median aerodynamic diameter of less than 5 µm, and
   wherein the salt of the drug amine has a decomposition index of less than 0.10.

2. The condensation aerosol of claim 1, wherein the particles comprise less than 5 percent by weight of drug amine degradation products.

3. The condensation aerosol of claim 2, wherein the condensation aerosol has a mass median aerodynamic diameter in the range of 1 to 5 µm.

4. The condensation aerosol of claim 3, wherein the condensation aerosol has a mass median aerodynamic diameter in the range of 1 to 3 µm.

5. The condensation aerosol of claim 1, wherein the salt of the amine drug is selected from the group consisting of: brompheniramine maleate, carbinoxamine maleate, chlorpheniramine maleate, cyproheptadine hydrochloride, pyrilamine maleate, buproprion hydrochloride, trimipramine maleate, tranylcypromine hydrochloride, protriptyline hydrochloride, apomorphine diacetate hydrochloride, buprenorphine hydrochloride, nicotine dihydrochloride, nicotine sulfate, apomorphine hydrochloride, diphenhydramine hydrochloride, mexiletine hydrochloride, and nicotine hydrochloride.

6. The condensation aerosol of claim 1, wherein the coating has a thickness within the range of 0.05 µm to 50 µm.

7. The condensation aerosol of claim 6, wherein the coating has a thickness within the range of 0.2 µm to 20 µm.

8. The condensation aerosol of claim 1, wherein the drug amine salt has a molecular weight within the range of 200 to 600.

9. The condensation aerosol of claim 1, wherein the condensation aerosol is formed at a rate greater than $10^9$ particles per second.

10. The condensation aerosol of claim 1, wherein the composition that is heated comprises at least 10 percent by weight of the salt of the drug amine.

11. The condensation aerosol of claim 10, wherein the composition that is heated comprises at least 90 percent by weight of the salt of the drug amine.

12. The condensation aerosol of claim 3, wherein the geometric standard deviation around the mass median aerodynamic diameter is less than 3.

13. A method of delivering a condensation aerosol of a drug amine, wherein the method comprises:
   a) heating a coating of a composition comprising a drug amine salt on a substrate to produce a drug amine vapor, wherein the drug amine salt has a decomposition index of less than 0.10; and
   b) condensing the vapor to form an aerosol,
   wherein the aerosol comprises particles comprising less than 10 percent by weight drug amine degradation products, and wherein the condensation aerosol has a mass median aerodynamic diameter of less than 5 μm.

14. The method of claim 13, wherein the particles comprise less than 5 percent by weight drug amine degradation products.

15. The method of claim 13, wherein the condensation aerosol has a mass median aerodynamic diameter within the range of 1 to 5 μm.

16. The method of claim 15, wherein the condensation aerosol has a mass median aerodynamic diameter within the range of 1 to 3 μm.

17. The method of claim 13, wherein the drug amine salt is selected from the group consisting of: brompheniramine maleate, carbinoxamine maleate, chlorpheniramine maleate, cyproheptadine hydrochloride, pyrilamine maleate, buproprion hydrochloride, trimipramine maleate, tranylcypromine hydrochloride, protriptyline hydrochloride, apomorphine diacetate hydrochloride, buprenorphine hydrochloride, nicotine dihydrochloride, nicotine sulfate, apomorphine hydrochloride, diphenhydramine hydrochloride, mexiletine hydrochloride, and nicotine hydrochloride.

18. The method of claim 13, wherein the coating has a thickness within the range of 0.05 μm to 50 μm.

19. The method of claim 18, wherein the coating has a thickness within the range of 0.2 μm to 20 μm.

20. The method of claim 13, wherein the drug amine salt has a molecular weight within the range of 200 to 600.

21. The method of claim 13, wherein the condensation aerosol is formed at a rate greater than $10^9$ particles per second.

22. The method of claim 13, wherein the composition that is heated comprises at least 10 percent by weight of the salt of the drug amine.

23. The method of claim 22, wherein the composition that is heated comprises at least 90 percent by weight of the salt of the drug amine.

24. The method of claim 15, wherein the geometric standard deviation around the mass median aerodynamic diameter is less than 3.

25. A condensation aerosol for delivery of a drug amine formed by heating a coating of a composition comprising a salt of the drug amine on a substrate, to produce a vapor, and cooling the vapor to form a condensation aerosol comprising particles,
wherein the drug amine is liquid in its free base form,
wherein the particles comprise at least 10 percent by weight of the drug amine and less than 10 percent by weight of drug amine degradation products,
wherein the condensation aerosol has a mass median aerodynamic diameter of less than 5 μm, and
wherein the salt of the drug amine has a decomposition index of less than 0.10.

26. A condensation aerosol of claim 25, wherein the particles comprise less than 5 percent by weight of drug amine degradation products.

27. A condensation aerosol of claim 26, wherein the condensation aerosol has a mass median aerodynamic diameter in the range of 1 to 5 μm.

28. The condensation aerosol of claim 27, wherein the condensation aerosol has a mass median aerodynamic diameter in the range of 1 to 3 μm.

29. The condensation aerosol of claim 27, wherein the geometric standard deviation around the mass median aerodynamic diameter is less than 3.

30. The condensation aerosol of claim 25, wherein the salt of the amine drug is selected from the group consisting of: brompheniramine maleate, carbinoxamine maleate, chlorpheniramine maleate, cyproheptadine hydrochloride, pyrilamine maleate, buproprion hydrochloride, trimipramine maleate, tranylcypromine hydrochloride, protriptyline hydrochloride, apomorphine diacetate hydrochloride, buprenorphine hydrochloride, nicotine dihydrochloride, nicotine sulfate, apomorphine hydrochloride, diphenhydramine hydrochloride, mexiletine hydrochloride, and nicotine hydrochloride.

31. The condensation aerosol of claim 25, wherein the coating has a thickness within the range of 0.05 μm to 50 μm.

32. The condensation aerosol of claim 31, wherein the coating has a thickness within the range of 0.2 μm to 20 μm.

33. The condensation aerosol of claim 25, wherein the drug amine salt has a molecular weight within the range of 200 to 600.

34. The condensation aerosol of claim 25, wherein the condensation aerosol is formed at a rate greater than $10^9$ particles per second.

35. The condensation aerosol of claim 25, wherein the composition that is heated comprises at least 10 percent by weight of the salt of the drug amine.

36. The condensation aerosol of claim 35, wherein the composition that is heated comprises at least 90 percent by weight of the salt of the drug amine.

37. A method of delivering a condensation aerosol of a drug amine, wherein the method comprises:
a) heating a coating of a composition comprising a drug amine salt on a substrate to produce a drug amine vapor, wherein the drug amine is a liquid in its free base form, and wherein the drug amine salt has a decomposition index of less than 0.10; and
b) condensing the vapor to form an aerosol,
wherein the aerosol comprises particles comprising less than 10 percent by weight drug amine degradation products, and
wherein the aerosol has a mass median aerodynamic diameter of less than 5 μm.

38. The method of claim 37, wherein the particles comprise less than 5 percent by weight drug amine degradation products.

39. The method of claim 38, wherein the condensation aerosol has a mass median aerodynamic diameter within the range of 1 to 5 μm.

40. The method of claim 39, wherein the condensation aerosol has a mass median aerodynamic diameter within the range of 1 to 3 μm.

41. The method of claim 39, wherein the geometric standard deviation around the mass median aerodynamic diameter is less than 3.

42. The method of claim 37, wherein the drug amine salt is selected from the group consisting of: brompheniramine maleate, carbinoxamine maleate, chlorpheniramine maleate, cyproheptadine hydrochloride, pyrilamine maleate, buproprion hydrochloride, trimipramine maleate, tranylcypromine hydrochloride, protriptyline hydrochloride, apomorphine diacetate hydrochloride, buprenorphine hydrochloride, nicotine dihydrochloride, nicotine sulfate, apomorphine hydrochloride, diphenhydramine hydrochloride, mexiletine hydrochloride, and nicotine hydrochloride.

43. The method of claim 37, wherein the coating has a thickness within the range of 0.05 μm to 50 μm.

44. The method of claim 43, wherein the coating has a thickness within the range of 0.2 μm to 20 μm.

45. The method of claim 37, wherein the drug amine salt has a molecular weight within the range of 200 to 600.

46. The method of claim 37, wherein the condensation aerosol is formed at a rate greater than $10^9$ particles per second.

47. The method of claim 37, wherein the composition that is heated comprises at least 10 percent by weight of the salt of the drug amine.

48. The method of claim 47, wherein the composition that is heated comprises at least 90 percent by weight of the salt of the drug amine.

49. A kit for delivering a condensation aerosol of a drug amine, wherein the kit comprises:
   a) a layer containing a salt of the drug amine coated on a solid support; and
   b) a device for providing the condensation aerosol, wherein the condensation aerosol is formed by heating the layer to produce a vapor of the drug amine, and condensing the vapor to form a condensation aerosol comprising particles,
   wherein the particles comprise less than 10 percent by weight drug amine degradation products,
   wherein the aerosol has an MMAD of less than 5 μm, and
   wherein the salt of the drug amine has a decomposition index of less than 0.10.

50. The kit according to claim 49, wherein the device comprises:
   a) a flow-through enclosure containing the solid support;
   b) a power source that can be activated to heat the solid support; and
   c) at least one portal through which air can be drawn by inhalation,
   wherein activation of the power source is effective to produce a vapor of the drug amine, and drawing air through the enclosure is effective to condense the vapor to form the condensation aerosol.

51. The kit according to claim 49, wherein the aerosol has an MMAD within the range of 1 to 5 μm.

52. The kit according to claim 49, wherein the aerosol has an MMAD of less than 3 μm.

53. The kit according to claim 52, wherein the aerosol has an MMAD within the range of 1 to 3 μm.

54. The kit according to claim 49, wherein peak plasma drug amine concentration is reached in less than 0.1 hours.

\* \* \* \* \*